(12) United States Patent
Gandhi

(10) Patent No.: US 11,033,653 B1
(45) Date of Patent: Jun. 15, 2021

(54) SMART SANITIZING RESPIRATOR

(71) Applicant: Raj K. Gandhi, Atlanta, GA (US)

(72) Inventor: Raj K. Gandhi, Atlanta, GA (US)

( * ) Notice: Subject to any disclaimer, the term of this patent is extended or adjusted under 35 U.S.C. 154(b) by 0 days.

(21) Appl. No.: 15/931,345

(22) Filed: May 13, 2020

(51) Int. Cl.
| | | |
|---|---|---|
| *A61L 9/20* | (2006.01) | |
| *A61M 16/08* | (2006.01) | |
| *A61M 16/06* | (2006.01) | |
| *A61M 16/20* | (2006.01) | |

(52) U.S. Cl.
CPC .......... *A61L 9/20* (2013.01); *A61M 16/0683* (2013.01); *A61M 16/0875* (2013.01); *A61M 16/208* (2013.01); *A61L 2209/12* (2013.01); *A61M 2202/0208* (2013.01)

(58) Field of Classification Search
None
See application file for complete search history.

(56) References Cited

U.S. PATENT DOCUMENTS

| | | | | | |
|---|---|---|---|---|---|
| 5,165,395 | A | * | 11/1992 | Ricci .................. | A41D 13/1146 128/202.22 |
| 7,114,497 | B2 | * | 10/2006 | Aylsworth ............ | A61M 16/00 128/204.18 |
| 10,506,861 | B1 | * | 12/2019 | Ma ......................... | A45D 29/18 |
| 2004/0033739 | A1 | * | 2/2004 | Courtney ................ | B63C 9/155 441/88 |
| 2005/0011523 | A1 | * | 1/2005 | Aylsworth ........ | A61M 16/0069 128/207.18 |
| 2010/0150793 | A1 | * | 6/2010 | Chan .................. | B01D 53/8687 422/186.3 |
| 2016/0121072 | A1 | * | 5/2016 | Smith ............... | A61M 16/0683 128/206.21 |
| 2016/0184539 | A1 | * | 6/2016 | Suzuki .................. | F04D 29/664 128/205.25 |

(Continued)

FOREIGN PATENT DOCUMENTS

| | | | | |
|---|---|---|---|---|
| CN | 201193284 | Y | * | 2/2009 |
| CN | 201912504 | U | * | 8/2011 |

(Continued)

OTHER PUBLICATIONS

Frequently Asked Questions / American Ultraviolet, retrieved from https://www.americanultraviolet.com/uv-germicidal-solutions/faq-germicidal.cfml , on Jun. 15, 2020.

(Continued)

*Primary Examiner* — Andrew Smyth
(74) *Attorney, Agent, or Firm* — Pabst Patent Group LLP

(57) ABSTRACT

A respirator assembly comprising a face mask fitting snugly over the mouth and nose, allowing little to no air leakage; at least two flexible connecting tubes coming out of the upper front part of the mask, an inspiratory line and an expiratory line, wherein the inspiratory line is connected to a one-way valve which allows air to flow in for inspiration and closes during expiration, and the expiratory line is connected to a one-way valve which allows the air to flow out during expiration and closes during inspiration; connected to a sanitizing chamber, wherein each sanitizing chamber comprises a means of emitting ultraviolet light and a power source, wherein the sanitizing chambers have ports to the exterior which are covered by material formed of or equivalent to surgical masks.

14 Claims, 1 Drawing Sheet

(56) References Cited

U.S. PATENT DOCUMENTS

2018/0036503 A1\* 2/2018 Mohamed ......... A61M 16/0666
2018/0045400 A1\* 2/2018 Bushee ................. F21V 3/0625
2020/0101183 A1\* 4/2020 Dijkstra ................... A61L 2/10

FOREIGN PATENT DOCUMENTS

CN 111053979 A \* 4/2020
JP 2010244854 A \* 1/2010
JP 2010244854 A \* 10/2010

OTHER PUBLICATIONS

Nakamura, et al., Sterilization Efficacy of Ultraviolet Irradiation on Microbial Aerosols Under Dynamic Airflow by Experimental Air Conditioning Systems, Bull Tokyo Med. Dent. Univ., 34(2):25-40 (1987).

University of California-Santa Barbara. "Ultraviolet LEDs prove effective in eliminating coronavirus from surfaces and, potentially, air and water", ScienceDaily. ScienceDaily, Apr. 14, 2020. Retrieved from www.sciencedaily.com/releases/2020/04/200414173251.htm, on Jun. 15, 2020.

Welch, et al., "Far-UVC light: A new tool to control the spread of airborne-mediated microbial diseases", Scientific Reports, 8(2752): 1-7 (2018).

\* cited by examiner

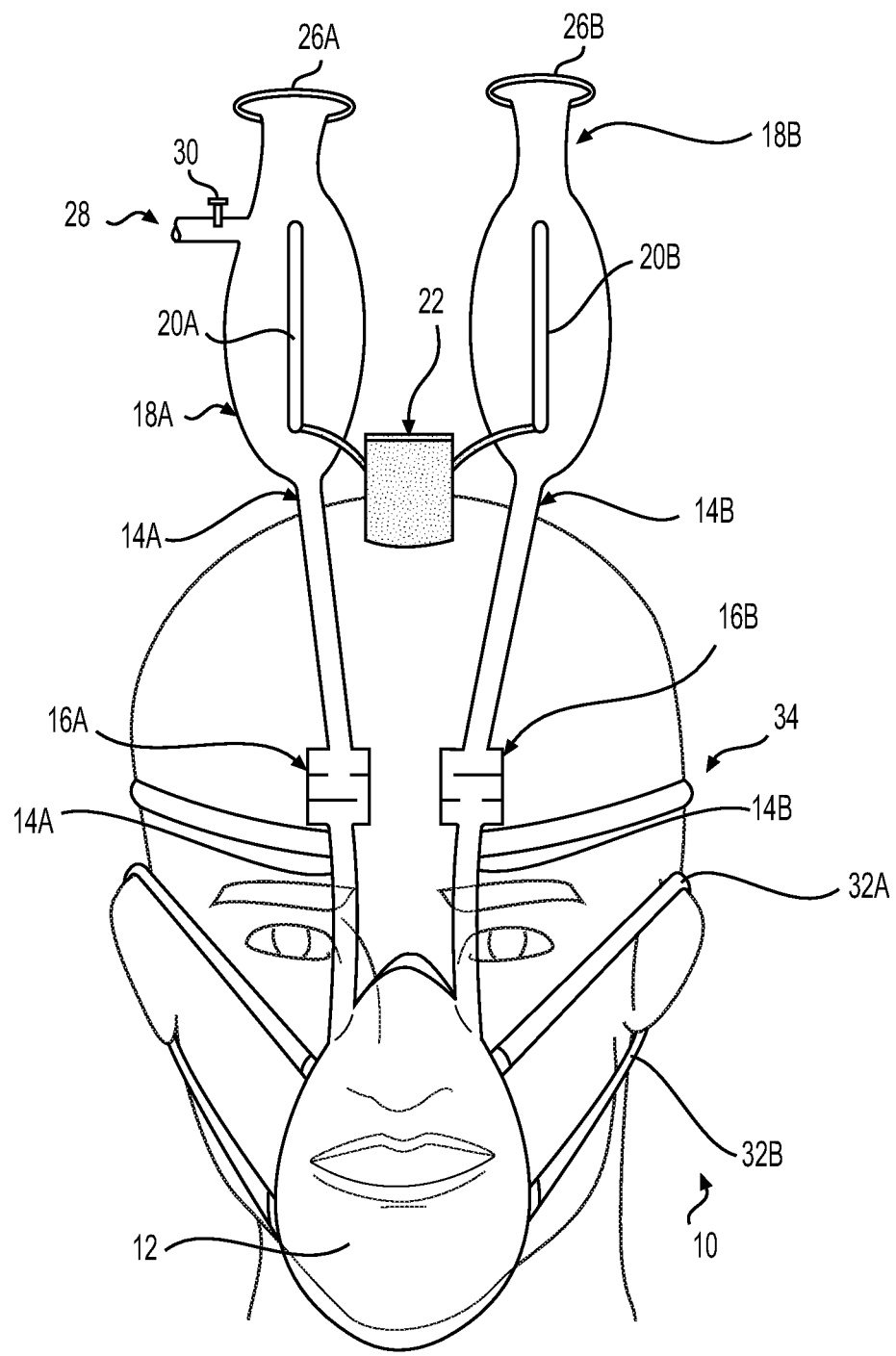

SMART SANITIZING RESPIRATOR

FIELD OF THE INVENTION

This invention is generally in the field of "smart", portable and inexpensive sanitizing respirators.

BACKGROUND OF THE INVENTION

A smart sanitizing respiratory device should be able to sanitize and disinfect each breath before you breath-in, and it should also disinfect and sanitize each breath you breathe out before it is discharged into the atmosphere.

It should be light and easy to wear, almost like a face mask.

Such a device will obviate the need for isolation and quarantine, especially of large masses in cruise ships or military bases. If you are sick with an acute respiratory infection, you will stay at home if the illness is mild or moderate and in the hospital if it is severe. If you have been exposed to Corona Virus or suspected of having been exposed but have no symptoms you should be able to go about your normal business while wearing this device. The same should apply if the symptoms are mild and/or infection is with "flu" or common cold virus.

This device would allow schools to stay open, with no need to close a town, city, a region or an entire country. The anxiety and fear will be minimized. Healthcare workers will greatly benefit from this device and will not have to wear suffocating masks like N-95 respirator.

It is an object of the present invention to provide a light weight, flexible respirator having a means for trapping bacterial and viral particles from entering or leaving the respirator.

It is an object of the present invention to provide a smart respirator that is easily and inexpensively manufactured, using standard equipment.

SUMMARY OF THE INVENTION

A respirator has been developed which is light weight and flexible, and provides a means to trap and kill bacterial and viral particles after they have been exhaled, before they are released into the air. As shown in FIG. 1, the respirator 10 includes the following features:

A face mask 12. The mask is light weight, soft and pliable. It fits snugly over the mouth and nose, allowing nearly zero air-leak around it.

Connecting tubes 14a, 14b. There are at least two flexible tubes coming out of the upper front part of the mask, labeled "Inspiratory line" 14a and "Expiratory line" 14b. These go vertically up over the forehead and curve around the frontal part of the skull going backward on the top of the skull. The Inspiratory line 14a is connected to a one-way valve 16a which allows air to flow in for inspiration. This valve 16a closes during expiration. The Expiratory line is connected to a one-way valve 16b which allows the air to flow out during expiration. This valve 16b closes during inspiration.

The tubes 14a, 14b are each connected to a very light weight oblong flask 18a, 18b referred to as a "Sanitizing Chamber". Each sanitizing chamber 18a, 18b is identified as inspiratory or expiratory based on its connection. Each sanitizing chamber 18a, 18b is about six to ten inches tall and preferably has the shape of a flask or cylinder and an internal volume of about 1500 milliliters.

In the center of each chamber there is a low voltage light fixture holding a long thin bulb 20a, 20b that will emit ultraviolet-c light when turned on. The bulb 20a, 20b may be a light emitting diode that releases light in the ultraviolet range, for example, between 100 and 280 nm. A battery 22 can be used to power the light. Hearing aid batteries should be sufficient to power LEDs. This light 20a, 20b continually sterilizes the air inside the sanitizing chambers 18a, 18b. The interior walls of the sanitizing chambers 18a, 18b are reflective, for example, being foil lined or having a reflective membrane on the inner surface, to maximize the light sterilizing effect.

The tops 24a, 24b of the sanitizing chambers 18a, 18b are open. These are preferably covered with surgical masks 26a, 26b, preferably made out of triple layer of cotton gauze. The masks 26a, 26b will be changed every eight hours when in use. For extra safety during an epidemic or high flu season, a double mask cover can be used.

The inspiratory chamber 18a has a side port 28 with an on and off stopper 30 on it. This port 28 is used for delivery of oxygen and/or medications if needed.

The mask 12 is held in place by straps 32a, 32b, extending from the face mask 12 around the ears, and a strap 34 that extends around the head and secures to the inspiratory lines 14a, 14b.

BRIEF DESCRIPTION OF THE DRAWINGS

FIG. 1 is a schematic of the sanitizing respirator positioned on a head, where the inspiratory and expiratory are shown in vertical juxtaposition, rather than resting on the top and back of the head.

DETAILED DESCRIPTION OF THE INVENTION

Some of the important aspects of the respirator include:

(1) Completely separate inspiratory air from the expiratory air, with the help of a face mask tightly fitted around the mouth and nose and two tubes and one way valves.

(2) The inspiratory air for each breath is held in a reservoir where all the bacteria and viruses in it are killed using ultraviolet-C light before it can be inhaled.

(3) The expired air of each breath is held in a reservoir and where it is disinfected by ultraviolet-C light before it is released into the ambient air.

As shown in FIG. 1, the respirator 10 includes the following features:

Face mask 12.

The mask is light weight, soft and pliable. It is preferably formed of a film forming or extrudable polymer such as a silicone or polypropylene, what is also biocompatible for use in contact with a human face, as determined by the US Food and Drug Authority (FDA). It should fit snugly over the mouth and nose, allowing nearly zero air-leak around it. The mask may have an involuted edge or gasket-type lining to insure greater air-tightness. The mask is preferably shaped to contour the nose, the forehead or cheekbones under the eyes, and the mouth, but may also be formed of a simple dome covering the nose and mouth.

Connecting Tubes

There are at least two flexible tubes coming out of the upper front part of the mask, labeled "Inspiratory line" 14a and "Expiratory line" 14b. These go vertically up over the forehead and curve around the frontal part of the skull going backward on the top of the skull. The tubes are formed of a flexible material such as a polypropylene. The Inspiratory line 14a is connected to a one-way valve 16a which allows air to flow in for inspiration. This valve 16a closes during expiration. The valve may be a simple one way flap valve, such as a membrane that moves inwardly for the inspiratory line 14a and outwardly (relative to the mouth and nose) for the expiratory line 14b. The Expiratory line is connected to a one-way valve 16b which allows the air to flow out during expiration. This valve 16b closes during inspiration.

Sanitizing Chamber

The tubes 14a, 14b are each connected to very light weight oblong flasks or bags 18a, 18b referred to as a "Sanitizing Chamber". Each sanitizing chamber 18a, 18b is identified as inspiratory or expiratory based on its connection. Each sanitizing chamber 18a, 18b is about six to ten inches tall and preferably has the shape of a flask or cylinder, and an internal volume of between about 300 to 2500 ml, preferably for an adult of about 1500 milliliters. Sanitizing chambers are made of a lightweight flexible material such as silastic or rubber.

The sanitizing chambers 18a, 18b may include a reflective lining, or may be formed of a reflective metal or polymeric material, which forms the chamber or lining thereof.

The sanitizing chambers may be in the shape of a flask, bottle, cylinder, tube or some other form of container and may have one or two ultraviolet-C lights therein, as discussed below, but each must have enough capacity to hold a volume of air equal to three times the tidal volume, so that the air is exposed to the ultraviolet-C light for a minimum of 10 seconds to achieve sterilization before it is inhaled. The same applies to the exhaled air.

The face mask assembly is worn over the mouth and nose and, in the preferred embodiment, the connecting tubes and one way valves go up on the forehead and the sanitizing chambers stand erect on the top of a cap over the head and/or are held in place with a strap around the forehead. Variations include where the sanitizing chamber has the shape of a right angle tube with a horizontal portion going from the front of the head to the back where it will turn up into a vertical portion. Alternatively, the chamber may be connected to or be in the form of a round or a convoluted tube. Other variations include carrying the assembly of the sanitizing chambers in a back pack or each sanitizing chamber on a shoulder.

Ultraviolet Light for Sterilization of the Sanitizing Chamber

In the center of each chamber 18a, 18b there is a low voltage light fixture holding a long thin bulb 20a, 20b or a single unit such as a light emitting diode (LED) that will emit ultraviolet-c light when turned on. The bulb 20a, 20b may be a light emitting diode that releases light in the ultraviolet range, for example, between 100 and 280 nm. A battery(ies) 22 can be used to power the light. Hearing aid batteries should be sufficient to power LEDs. Incandescent ultraviolet lights may require one or two AA or AAA batteries. These can be rechargeable lithium batteries. The lights 20a, 20b continually sterilize the air inside the sanitizing chambers 18a, 18b. The respirator assembly should include means to turn the light on or off from outside the sterilizing chamber. The light and/or power supply may be located inside or outside of the respirator assembly. In the preferred embodiment including a sterilizing light, the interior walls of the sanitizing chambers 18a, 18b are reflective, for example, being foil lined or having a reflective membrane on the inner surface, to maximize the light sterilizing effect.

Surgical Mask Coverings

The tops 24a, 24b of the sanitizing chambers 18a, 18b are open. These are preferably covered with surgical masks 26a, 26b, preferably made out of triple layer of cotton gauze. The masks 26a, 26b will be changed every eight hours when in use. For extra safety during an epidemic or high flu season, a double mask cover can be used.

A surgical mask is a loose-fitting, disposable device that creates a physical barrier between the mouth and nose of the wearer and potential contaminants in the immediate environment. Surgical masks are regulated under 21 CFR 878.4040. Surgical masks are made in different thicknesses and with different ability to protect from contact with liquids. These properties may also affect how easily one can breathe through the face mask and how well the surgical mask protects the wearer.

If worn properly, a surgical mask is meant to help block large-particle droplets, splashes, sprays, or splatter that may contain viruses and bacteria, keeping it from reaching your mouth and nose. Surgical masks may also help reduce exposure of your saliva and respiratory secretions to others.

An N95 respirator is a respiratory protective device designed to achieve a very close facial fit and very efficient filtration of airborne particles. The 'N95' designation means that when subjected to careful testing, the respirator blocks at least 95 percent of very small (0.3 micron) test particles. If properly fitted, the filtration capabilities of N95 respirators exceed those of face masks.

Size of Sanitizing Chambers

An average healthy adult male breaths in and breaths out about 500 milliliters of air with each breath and at rest his respiratory rate is about 12 to 15 breaths per minute. At the rate of 15 breaths per minute, he takes in 500 milliliters of air every four seconds or so, and exhales the same volume every four seconds. The sanitizing chamber of this respirator will hold about 300 to 2500 milliliters of air, preferably 1500 milliliters of air from which 500 milliliters will be inhaled every four seconds and replaced by the same amount of atmospheric air filtered through the surgical mask, discussed below. If the sanitizing chamber was smaller and could hold only 500 milliliters, the air being inhaled would be exposed to ultraviolet light only for four seconds before being inhaled. This will be too short to achieve satisfactory sanitization. Ultraviolet light takes 10 to 15 seconds to sterilize the air in its vicinity. With 1500 milliliters of air in the sanitizing chamber, each breath of 500 milliliters would have been exposed to ultraviolet light for at least 12 seconds before being inhaled. For men, sanitizing chambers of 2000 or even 2500 milliliters capacity are better.

An average healthy adult female breaths in and breaths out about 400 milliliters of air with each breath at rest, and her respiratory rate is about 14 to 15 per minute. With mild exercise like slow walk during grocery shopping it may go up to 18 to 20 per minute. Therefore a sanitizing chamber of 1500 milliliters will be sufficient and adequate for the average woman.

Sanitizing chambers can be provided in multiple sizes, typically between 300 ml for a small child to 2500 for a very large adult. These can be formed as an integral unit with the Mask 12 or connected to the inspiratory lines 14a, 14b, to provide maximum flexibility in sizes. Smaller sizes can be made for children, with smaller sanitizing chamber 18a, 18b.

Port

The inspiratory chamber 18a has a side port 28 with an on and off stopper 30 on it. This port 28 is used for delivery of oxygen and/or medications if needed. The port may be a standard type port with a rubber stopper of the type used with catheters or IV drips, or may be a removable or openable cap, stopper or comparable cover for a small opening into the inspiratory chamber 18a.

Variants in the Respirator and Methods of Manufacture

In one embodiment, the face mask, tubes and one way valves can be made as a single integral part using lightweight transparent silastic or other flexible plastic.

The respiratory reservoirs or chambers along with the ultraviolet light holding fixtures can be made as a second integral part using lightweight aluminum.

A third integral part can include the power source and the connections held together in a lightweight plastic case.

The surgical mask or its equivalent to cover the open end of the sanitizing chamber is formed as a fourth integral part.

Straps to Secure the Respirator

The mask 12 is held in place by straps 32a, 32b, extending from the face mask 12 around the ears, and a strap 34 that extends around the head and secures to the inspiratory lines 14a, 14b.

These typically are elastic and formed of rubber or fabric coated rubber.

Methods of Using and Advantages of the Respirator

There are a number of advantages to using this device. The air going into the lungs of the user will be first filtered by the surgical and then sterilized by the ultraviolet light. It will also enter the sanitizing chamber at a higher level where the air would be relatively clean and free of droplets hanging up in the air. So if the user is healthy and is worried about catching an airborne infection like corona virus, in a public location such as a restaurant or grocery store, he/she will need to turn the light on in the inspiratory chamber. Since he is healthy and poses no risk to the environment, he can leave the expiratory chamber light off. Preferably the ultraviolet lights are in use in public places. Since most people are healthy and will be using these respirators prophylactically, they will be sanitizing the air continually with each breath, thus helping the environment.

This respirator will also provide some therapeutic benefits. Supplemental oxygen can be given easily through the side port of the inspiratory chamber without wasting any oxygen into the atmosphere as happens with nasal cannula or a face mask. Someone with a respiratory rate of 20 per minute and tidal volume of 500 milliliters, will be breathing in and out 10 liters of air every minute. Oxygen through the side port of the inspiratory chamber at the rate of 1 liter per minute will supply 10% supplemental oxygen. At 2 liters per minute it will go up to 20% and so on.

In early stages of respiratory infection with corona virus perhaps this is all one would need in addition to other supportive measures. It will be possible to provide this kind of care at home to most patients, thus avoiding the need for hospitalization. Home health care workers, respiratory therapists, and nurses will be able to monitor the progress of such patients-mostly via telephone and sometimes by home visits if needed. Patients and their families can be trained easily to check their vital signs and even oxygen saturation on daily basis and report to their heath care provider. Only very seriously sick patients requiring mechanical ventilation and/or other intensive therapeutic measures will need hospitalization.

Additional benefits include using it to deliver oxygen and/or other therapeutic agents into the bronchopulmonary segments with greater efficiency than the modalities in use at present. For this purpose a regular version of the smart respirator without ultraviolet lights. This device should also be used as a prophylactic treatment of other respiratory ailments like bronchial asthma, allergies and emphysema.

The respirator is easy to clean. The only disposable component is the surgical mask covering the mouth of each sanitizing chamber. Even that can be washed and reused, especially if it is made of triple layer of cotton

REFERENCES

1. Welch, David; et al. (January 2018). "Far-UVC light: A new tool to control the spread of airborne-mediated microbial diseases". Scientific Reports. 8 (1): 2752. Bibcode:2018NatSR . . . 8.2752W. doi:10.1038/s41598-018-21058 w. ISSN 2045-2322. PMC 5807439. PMID 29426899.
2. Frequently Asked Questions/American Ultraviolet www.americanultraviolet.com>faqgermicid.
3. www.ncbi.nlm.nih.gov>pubmed; Sterilization efficacy of ultraviolet irradiation on microbial aerosols under dynamic airflow by experimental air conditioning systems. Nakamura H(1).
4. University of California-Santa Barbara. "Ultraviolet LEDs prove effective in eliminating coronavirus from surfaces and, potentially, air and water." ScienceDaily. ScienceDaily, 14 Apr. 2020. <www.sciencedaily.com/releases/2020/04/200414173251.htm>.
5. www.britannica.com>biography>Niels-Ryberg-Finsen

I claim:

1. A respirator assembly comprising a face mask fitting snugly over the mouth and nose, allowing little to no air leakage; at least two flexible connecting tubes connecting the face mask to a first inspiratory sanitizing chamber and to a second expiratory sanitizing chamber, wherein the first flexible connecting tube is an inspiratory line and the second flexible connecting tube is an expiratory line, the first and second flexible connecting tubes extending from the face mask up to two separate sanitizing chambers;

wherein the inspiratory line is connected to a one-way valve located in the flexible connecting tube between the inspiratory sanitizing chamber and the face mask, which allows air to flow in for inspiration and closes during expiration, and the expiratory line is connected to a one-way valve located in the flexible connecting tube between the expiratory sanitizing chamber and the face mask, which allows the air to flow out during expiration and closes during inspiration;

wherein each flexible connecting tube is connected to a separate sanitizing chamber, the sanitizing chambers having a volume of between 1500 ml and 2500 ml for adult human use, and being formed of a light weight gas impermeable material; and wherein each of the sanitizing chambers has a port to the exterior which is covered by material allowing air flow but restricting passage of air borne particles.

2. The respirator assembly of claim 1 comprising a battery powered light emitting diode for generating ultraviolet light.

3. The respirator assembly of claim 1 comprising a port in the inspiratory sanitizing chamber which can be closed and opened to insert liquid, gas or solid into the inspiratory sanitizing chamber.

4. The respirator assembly of claim 1 comprising means for securing the respirator assembly.

5. The respirator assembly of claim 1 wherein the sanitizing chambers have a volume of between 1500 and 2000 ml for adult human use.

6. The respirator assembly of claim 1 wherein the sanitizing chambers are formed of a light weight gas impermeable material having a reflective interior surface.

7. The respirator assembly of claim 1 wherein each sanitizing chamber, on the inside emits ultraviolet light having a wavelength between 100 and 280 nm.

8. The respirator assembly of claim 7 comprising a power source and switch for turning the ultraviolet light on and off from the exterior of the sanitizing chambers.

9. The respirator assembly of claim 7 wherein the ultraviolet light is emitted by a light emitting diode or bulb.

10. The respirator assembly of claim 1 comprising means for securing the respirator assembly to the face of a person.

11. The respirator assembly of claim 1 wherein the face mask is formed of silicone or polypropylene.

12. The respirator assembly of claim 1 wherein each sanitizing chamber is about six to ten inches tall.

13. The respirator assembly of claim 1 wherein each sanitizing chamber is formed of silastic or rubber.

14. The respirator assembly of claim 1 wherein the connecting tubes extend from the face mask over the forehead to connect with the sanitizing chambers.

\* \* \* \* \*